(12) United States Patent
Rossin et al.

(10) Patent No.: US 6,280,399 B1
(45) Date of Patent: Aug. 28, 2001

(54) SUBSTANCE DELIVERY DEVICE FOR USE WITH A PROCEDURE PERFORMING INSTRUMENT

(75) Inventors: Victor D. Rossin, Deerfield; Gregory C. Groenke, Gurnee; George Bourne, Libertyville, all of IL (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 09/167,478

(22) Filed: Oct. 6, 1998

(51) Int. Cl.[7] .................................................. A61B 10/01
(52) U.S. Cl. ........................................... 600/567; 604/131
(58) Field of Search ................................... 600/566, 567, 600/573, 579

(56) References Cited

U.S. PATENT DOCUMENTS

| | | | |
|---|---|---|---|
| D. 289,198 | 4/1987 | Karten ................................. D24/14 |
| D. 379,229 | 5/1997 | Como Rodriguez et al. ....... D24/146 |
| D. 379,515 | 5/1997 | Kuehn et al. ........................ D24/146 |
| 4,266,555 | 5/1981 | Jamshidi .............................. 128/753 |
| 4,356,828 | 11/1982 | Jamshidi ............................. 128/754 |
| 4,776,346 | 10/1988 | Beraha et al. ...................... 128/754 |
| 4,844,087 | * 7/1989 | Garg ................................... 600/566 |
| 4,907,598 | 3/1990 | Bauer ................................. 128/753 |
| 5,261,416 | 11/1993 | Taussig . | |
| 5,282,477 | 2/1994 | Bauer ................................. 128/754 |
| 5,313,958 | 5/1994 | Bauer ................................. 128/754 |
| 5,331,972 | 7/1994 | Wadhwani et al. ................. 128/754 |
| 5,476,102 | 12/1995 | Como et al. ....................... 128/754 |
| 5,505,210 | 4/1996 | Clement . | |
| 5,538,009 | 7/1996 | Bryne et al. ....................... 128/754 |
| 5,685,320 | * 11/1997 | Zimmon et al. .................... 600/579 |
| 5,725,506 | * 3/1998 | Freeman et al. ................... 600/579 |
| 5,758,655 | 6/1998 | Como Rodriguez et al. ....... 128/749 |
| 5,792,074 | 8/1998 | Turkel et al. . | |
| 5,916,175 | 6/1999 | Bauer ................................. 600/567 |

OTHER PUBLICATIONS

McEvoy RD, Percutaneous biopsy of intrapulmonary mass lesions experience with a disposable cutting needle, 1983.

* cited by examiner

*Primary Examiner*—Robert L. Nasser
*Assistant Examiner*—Pamela L. Wingood
(74) *Attorney, Agent, or Firm*—Andrew G. Rozycki; Andrea L. Wayda; Donald O. Nickey

(57) ABSTRACT

A device for delivering a substance such as a surgical sealant or adhesive to an internal portion of the body that has been acted on by a procedure performing instrument such as a catheter, trocar, laparoscopic instrument or a biopsy device is described. The invention more particularly relates to a biopsy device for obtaining one or more tissue samples and for applying at least one substance to the biopsy site in one operation.

22 Claims, 5 Drawing Sheets

SUBSTANCE DELIVERY DEVICE FOR USE WITH A PROCEDURE PERFORMING INSTRUMENT

BACKGROUND OF THE INVENTION

The present invention relates to a device for delivering a substance to an internal portion of a body that has been acted on by a procedure performing instrument such as a catheter, trocar, laparoscopic instrument or a biopsy device. The invention more particularly relates to a biopsy device for obtaining one or more tissue samples and for applying at least one substance to the biopsy site in one operation. The biopsy device is particularly adapted to remove a core or segment of tissue from the biopsy site and then apply a surgical adhesive comprised of a first component containing fibrinogen and a second component containing thrombin to the biopsy site to seal the site and control bleeding. If required, multiple tissue samples may be collected before applying the surgical adhesive. The biopsy device described may be operated manually or used in a semi-automatic or automatic mode. The biopsy device may also be adapted to remove a tissue sample from the biopsy site by aspiration.

An excision or coring biopsy is commonly carried out by inserting a needle such as that needle set disclosed in U.S. Pat. No. 3,477,423 into the organ or tissue to be biopsied. That needle is comprised of an outer hollow cutting cannula with an inner stylet needle having a semi-circular notch ground away at the distal end. As the stylet is advanced into the tissue, the tissue is pierced and relaxes or prolapses into the notched cut out or recess. When the cannula is slid forward, the tissue in the notch of the stylet is sliced off and retained in the notch until the cannula is drawn back. The needle yields a core tissue sample which is semi-circular in cross section with its length determined by the length of the notch.

An aspiration biopsy is commonly carried out using an aspiration device known as a Menghini needle as described in U.S. Pat. No. 4,850,373 which is hereby incorporated by reference in its entirety. A biopsy aspirating device is also described in U.S. Pat. No. 3,938,505 which is also incorporated by reference herein in its entirety. In an aspiration biopsy, the Menghini needle or other compatible soft-tissue biopsy aspirating device is directed to the biopsy site and positioned so that the distal end of the needle is located in the tissue or cyst to be biopsied. A syringe is then attached to the proximal end of the needle and tissue or fluid is aspirated from the site. The needle is then withdrawn.

Under certain circumstances, several complications can develop when biopsy samples are collected with known devices. For example, excision biopsies from lung tissue are associated with a relatively high complication rate due to hemorrhage and pneumothorax (McEvey, R. D., Bagley, M. D., Antic. R. 1983: Percutaneous Biopsy of Intrapulmonary Mass Lesions, Cancer 51, 2321). Profuse bleeding is also considered the most important complication associated with excision biopsies of the kidney and other organs. Profuse bleeding can be a particular problem during the biopsy of patients with hemophilia or other clotting disorders as well as those patients under treatment with anti-coagulants such as heparin or coumadin. Aspiration and core biopsies of the liver can also be complicated by profuse bleeding.

To minimize these possible complications, biopsy devices adapted to deliver a surgical adhesive to the biopsy site after aspiration or excision of a tissue sample have been developed. For example, U.S. Pat. No. 4,850,373 is directed to a manual aspiration biopsy device including a two- or multi-lumen biopsy cannula which has a biopsy channel of constant cross-section over its entire length and at least one application channel. On its proximal end, the device is provided with connection facilities for an aspiration device and at least one application device. At least one application channel is formed by a tube eccentrically slipped over the biopsy channel wall. After tissue is collected, a substance such as a blood coagulation material may be introduced directly to the biopsy site.

European Patent 0 455 626 is directed to a manual biopsy device for obtaining a tissue sample and for applying at least one substance in one operation. The biopsy device comprises a biopsy channel having a cutting edge for cutting off tissue and an application channel for applying a blood-clotting substance. The application channel is defined by an application tube slipped over the biopsy cannula. The front end of the application tube is rearwardly offset relative to the cutting edge of the biopsy cannula. At the opposite end of the application channel, a tightly joined connecting piece is provided for connecting at least one duct to convey the blood-clotting substance to the application channel. The biopsy device can be connected to a suction device to collect tissue samples by aspiration. Alternatively, the device can be adapted to perform excision biopsies by longitudinally displaceably mounting a needle with a tissue-penetrating tip within the biopsy cannula as illustrated in U.S. Pat. No. 3,477,423.

The design of the device disclosed in EP 0 455 626 has several potential drawbacks. The clearance between the inner wall of the application tube and the outer wall of the biopsy cannula is small. Consequently, when injecting a substance with a viscous component or components such as a fibrin sealant into the application channel, the user must exert substantial pressure on the injector device to force the components into the application channel for delivery to the biopsy site. As a result, tissue sealant can leak out from the connection between the injector device and the applicator tip. The surgical sealant can also leak out at the connection point between the applicator tip and the cantilevered portion of the connecting tube leading to the application channel.

A second potential drawback of the excision biopsy device disclosed in EP 0 455 626 is contamination of the biopsy sample with the surgical sealant. Since surgical sealant is injected through the application channel while the stylet is still in the biopsy cannula, surgical sealant flows back over the cored tissue sample contained within the biopsy cannula after the surgical sealant is delivered to the biopsy site. As a result, the biopsy sample becomes coated with the surgical sealant such as a fibrin tissue sealant thereby complicating any diagnosis based on analyis of the excised tissue sample.

Theoretically, sample contamination by tissue sealant in the excision biopsy device described in EP 0 455 626 could be avoided by withdrawing the stylet needle containing the excised tissue and the biopsy cannula from the device, leaving only the application tube in place. If the user determined that the tissue sample excised was not of sufficient size or quality for histological examination, the stylet needle could be re-inserted and additional samples obtained. When the biopsy was completed, surgical sealant could then be applied to the biopsy site through the relatively unconstricted application tube. However, withdrawal of the stylet needle/biopsy cannula assembly from the device would provide an unrestricted pathway for blood and sealant to flow back through the application tube by capillary action and severely compromise any attempt by the user to harvest additional biopsy samples or to seal off the biopsy site with a surgical sealant.

SUMMARY OF THE INVENTION

In accordance with the invention, a device is described for delivering a substance to an internal portion of a body which has been acted on by a procedure performing instrument such as a catheter, a trocar, a laparoscopic instrument or a biopsy device. The device includes an application tube having a proximal end, a distal end and an internal lumen for receiving the substance to be delivered and at least a portion of the procedure performing instrument. A housing assembly is disposed on the proximal end of the application tube and has an internal lumen extending from a proximal end of the housing assembly to a distal end of the housing assembly. The housing assembly lumen is in communication with the internal lumen of the application tube so as to define a flow passage A flow control member is disposed in the flow passage and has a first position that opens the flow passage and a second position that closes the flow passage.

A variety of substances including surgical sealants and adhesives can be delivered to an internal portion of the body using this device. In addition, the surgical sealants and adhesives can themselves act as matrices for the delivery of antibiotics, drugs and other therapeutic agents.

Preferably, the device of the invention is a device for obtaining a tissue sample from an internal portion of a body and for applying at least one substance to an internal portion of a body. The device comprises a biopsy cannula having an internal lumen and a distal cutting edge for cutting off tissue. A needle member is slideably mounted within the internal lumen and has a recess for receiving the tissue sample. A driver, which may be manually, semi-automically or automatically operable, is associated with the cannula and the needle member for effecting relative movement between the cannula and the needle and cutting of the tissue. An application tube having a proximal end, a distal end and an internal lumen is disposed around the cannula with the distal end of the application tube rearwardly offset relative to the cutting edge of the cannula. A housing assembly is sealingly engaged to the proximal end of the application tube. The housing assembly includes an internal lumen through which the cannula and needle are slidingly moveable. The housing assembly lumen is in communication with the internal lumen of the application tube so as to define a flow passage. A flow control member is disposed in the flow passage and has a first position that opens the flow passage and a second position that closes the flow passage.

In another embodiment, the device may be provided with a back housing which is engaged to the proximal end of the housing assembly and which is also engageable with the driver. The back housing includes a bore through which the cannula and the needle are slidingly moveable. A flow control member is positioned between the engagingly affixed proximal end of the housing assembly and the back housing to prevent backflow of flowable material. The biopsy cannula and the needle member are slidingly moveable through the flow control member.

In another embodiment of the invention, a device for obtaining a tissue sample from an internal portion of a body and for applying at least one substance to an internal portion of a body is provided as described above with a housing assembly that is sealingly engaged to the proximal end of the application tube which contains an internal lumen through which the biopsy cannula and needle member are slidingly moveable and a substance supply tube communicating with the internal lumen of the application tube which is engageable with a substance supply for applying the substance to the application tube.

In an alternate embodiment of the invention, the device for obtaining a tissue sample from an internal portion of a body and for applying at least one substance to an internal portion of a body comprises a Menghini needle or an equivalent soft tissue biopsy aspirating device as described in U.S. Pat. Nos. 4,850,373 and 3,938,505 respectively. The needle or aspirating device is attachable to a source of suction for aspiration of tissue or sample from the internal portion of a body. An application tube having a proximal end, a distal end and an internal lumen is disposed around the needle or aspirating device with the distal end of the application tube rearwardly offset relative to the cutting edge of the needle or aspirating device. A housing assembly is sealingly engaged to the proximal end of the application tube. The housing assembly includes an internal lumen through which the needle or aspirating device is slidingly moveable. The housing assembly lumen is in communication with the internal lumen of the application tube so as to define a flow passage. A flow control member is disposed in the flow passage and has a first position that opens the flow passage and a second position that closes the flow passage.

DETAILED DESCRIPTION OF THE PREFERRED EMBODIMENTS

Figure 1:
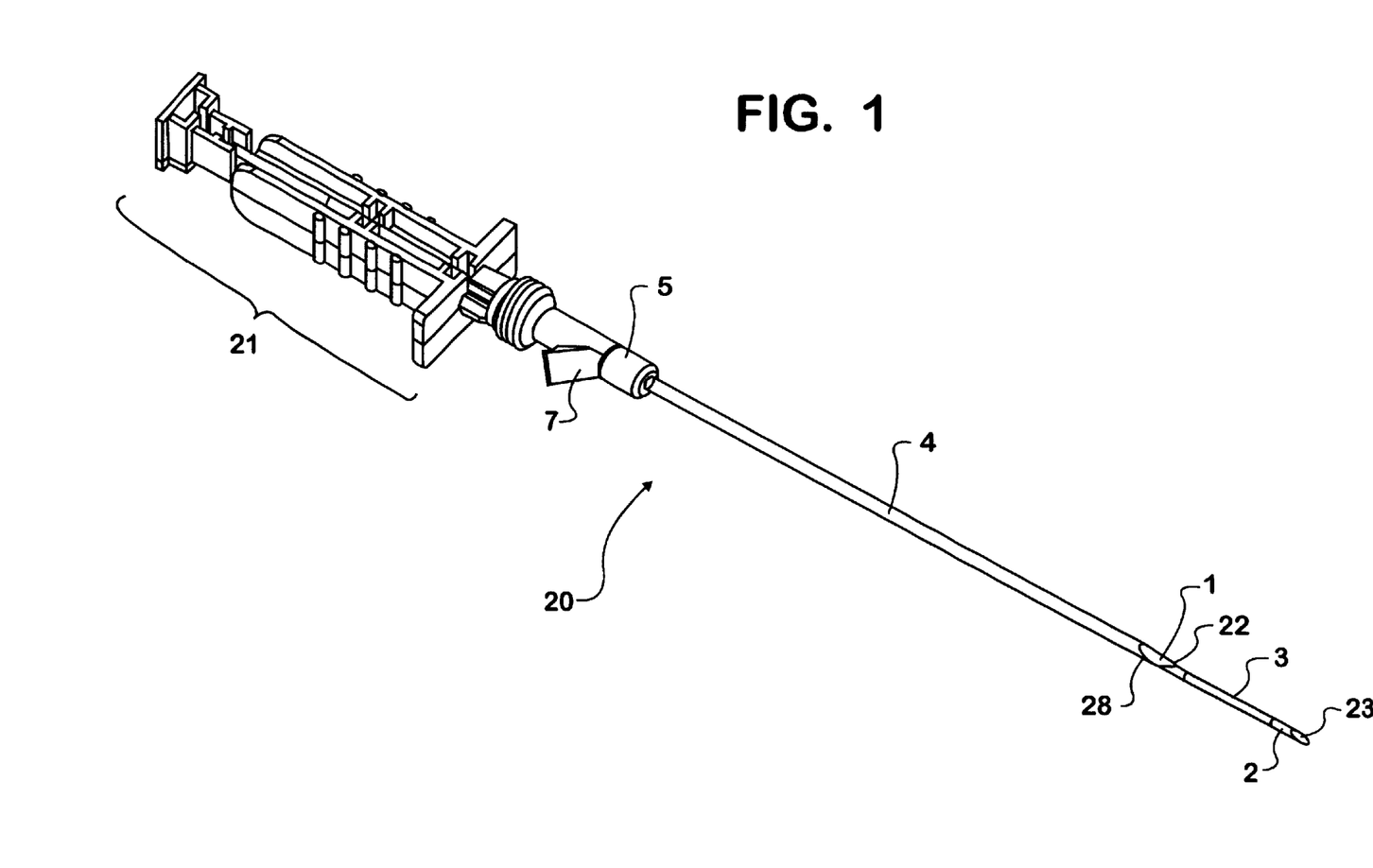
FIG. 1 is a perspective view of a manual biopsy device according to the invention.

Referring to FIG. 1, a manual biopsy device 20 of the present invention comprises a biopsy cannula 1 having an internal lumen which defines a biopsy channel and having a distal cutting edge 22 for shearing off tissue. Longitudinally displaceably mounted and concentric with biopsy cannula 1 is a needle member 2 having a distal cutting tip or a tissue-penetrating tip 23. Needle member 2 is provided with a recess 3 at its distal end so as to accomodate a tissue sample. The tissue sample recess 3 is displaceable from a position located within the biopsy cannula 1 to a position located outside of the biopsy cannula 1 and back using a driver 21 connected to the biopsy cannula 1 and the needle member 2. Driver 21 controls relative movement between the biopsy cannula 1 and the needle member 2 during tissue sample removal. An example of a manual biopsy needle set is set forth in U.S. Pat. No. 3,477,423 which is herein incorporated by reference in its entirety.

Figures 2, 3:
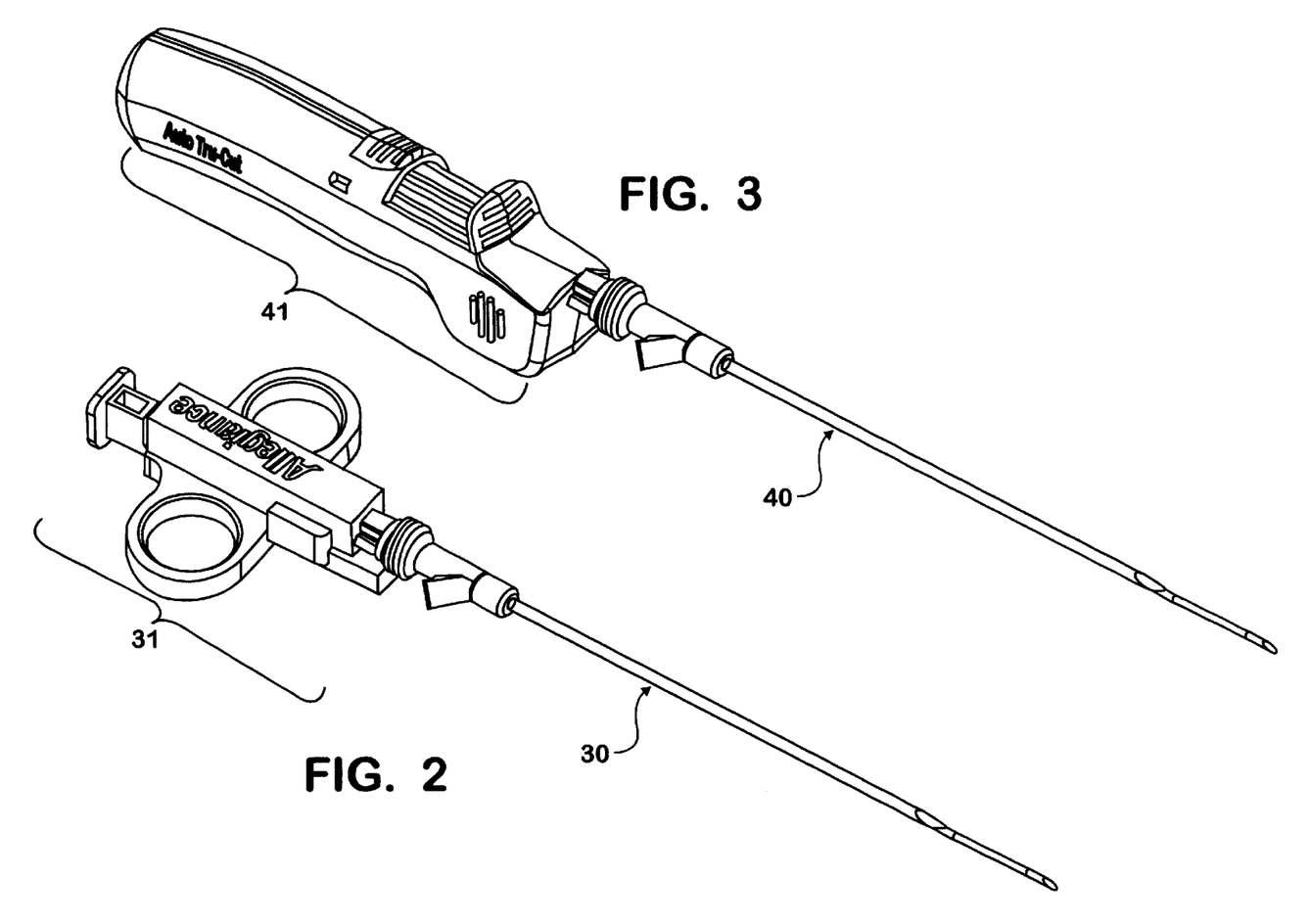
FIG. 2 is a perspective view of a semi-automatic biopsy device according to the invention.
FIG. 3 is a perspective view of an automatic biopsy device according to the invention.

FIGS. 2 and 3, respectively, illustrate a semi-automatic 30 and an automatic biopsy device 40 embodiment of the invention wherein relative movement between the biopsy cannula and the needle member during tissue sample removal is controlled using semi-automatic driver 31 and automatic driver 41 respectively. A description of the construction and operation of the driver of a semi-automatic biopsy device is described in U.S. Pat. No. 5,313,958. A description of the construction and operation of the driver of an automatic biopsy device is disclosed in U.S. Pat. Nos. 4,958,625, 4,944,308 and 5,172,702. These four patents are incorporated by reference herein in their entirety.

Referring again to FIG. 1, an application tube 4 having a proximal end, a distal end and an internal lumen is slipped over and concentrically positioned around the biopsy cannula 1 such that the biopsy cannula 1 and needle member 2 can be freely withdrawn through the application tube 4. The distal end of the application tube 4 is rearwardly offset relative to the cutting edge of the biopsy cannula 1 and terminates in a blunt cut end or an angled cutting surface 28. At the proximal end of the application tube 4, a housing assembly 5 is tightly joined by gluing or sealing.

Figure 4:
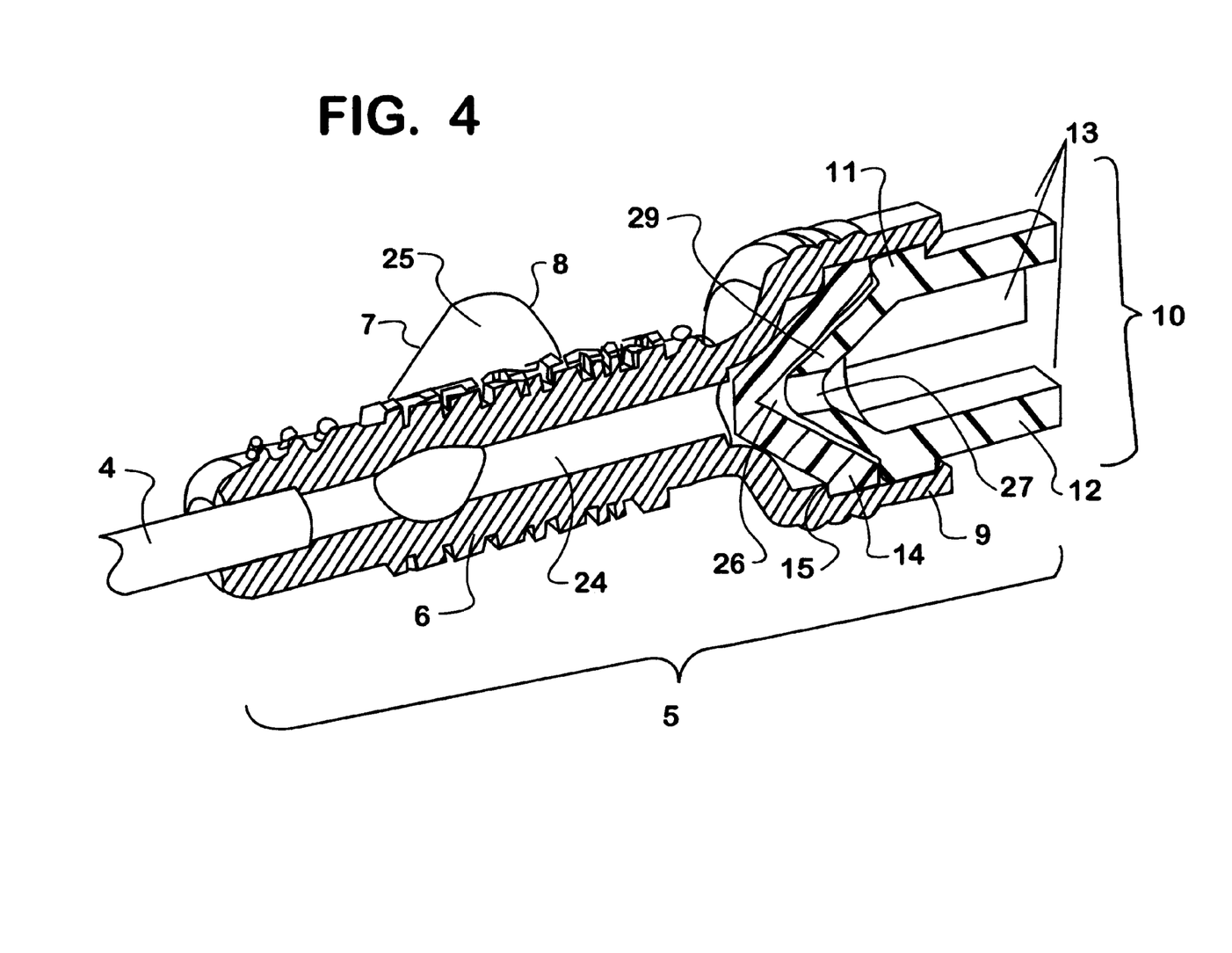
FIG. 4 is a sectioned view of the housing assembly of the biopsy device of FIG. 1.

Referring to FIG. 4, the housing assembly 5 includes a preferably straight tube portion 6 having an internal lumen 24 through which the biopsy cannula 1 and needle member 2 extend therethrough. A substance supply tube 7 enters into tube portion 6 of the housing assembly 5 and includes at least one lumen 25 leading into and communicating with the internal lumen 24 of the tube portion 6 so as to form a flow passage through which a substance can be delivered into the application tube 4 for application to the biopsy site Substance entry port 8 of substance supply tube 7 is fitted with a luer slip, luer lock or a similar type connection for lockingly engaging an applicator device (not shown) containing the substance to be applied to the biopsy site. As noted above, the application tube 4 is sealingly fixed to the distal end of the tube portion 6 of the housing assembly 5. The proximal end of the tube portion 6 preferably flares out to an integrally molded hub housing 9 having a central bore 26. Hub housing 9 preferably mates to a back housing 10 comprised of a central bore 27, a guide channel 29, a distal portion 11 for connection to the hub housing 9 and a proximal portion 12 comprising an interface 13 for engaging a mating surface on a manual, semi-automatic or automatic biopsy device driver. The interface 13 includes but is not limited to prongs, fingers and equivalent structures. Preferably, housing assembly tube portion 6, substance supply tube 7 and the hub housing 9 are molded as one piece. Alternatively, tube portion 6, substance supply tube 7 and hub housing 9 are bonded together using glue, adhesive or ultrasonic welding or equivalent bonding means. The housing assembly is preferably constructed of a hard plastic such as ABS (Lustran ) which can be machined into the shape required for the invention.

Interposed within the space created by the mating of the hub housing 9 and the back housing 10 is a flow control member 14, preferably a one-way valve which is positioned within the space so that it rests and is centered upon an annular shelf 15 molded on the interior wall of the hub housing 9. The flow control member 14 is always closed to the backflow of blood and surgical sealant and only opens when the biopsy cannula 1 containing the needle member 2 is withdrawn from the device. Guide channel 29 in back housing 9 positions the biopsy cannula 1 and the needle member 2 as they are inserted through the flow control member 14 so that the biopsy cannula 1 and the needle member 2 pass through the center of the flow control member 14 and do not shear off or otherwise damage the flow control member 14 while passing through it.

The flow control member 14 is preferably a rubber duck-bill valve. However, the flow control member 14 can also be replaced by any other device which allows the biopsy needle set comprised of the biopsy cannula 1 and the needle member 2 to be completely withdrawn from the device while simultaneously stopping any backflow of flowable material such as blood or tissue sealant from the proximal end of the device.

Figure 5:
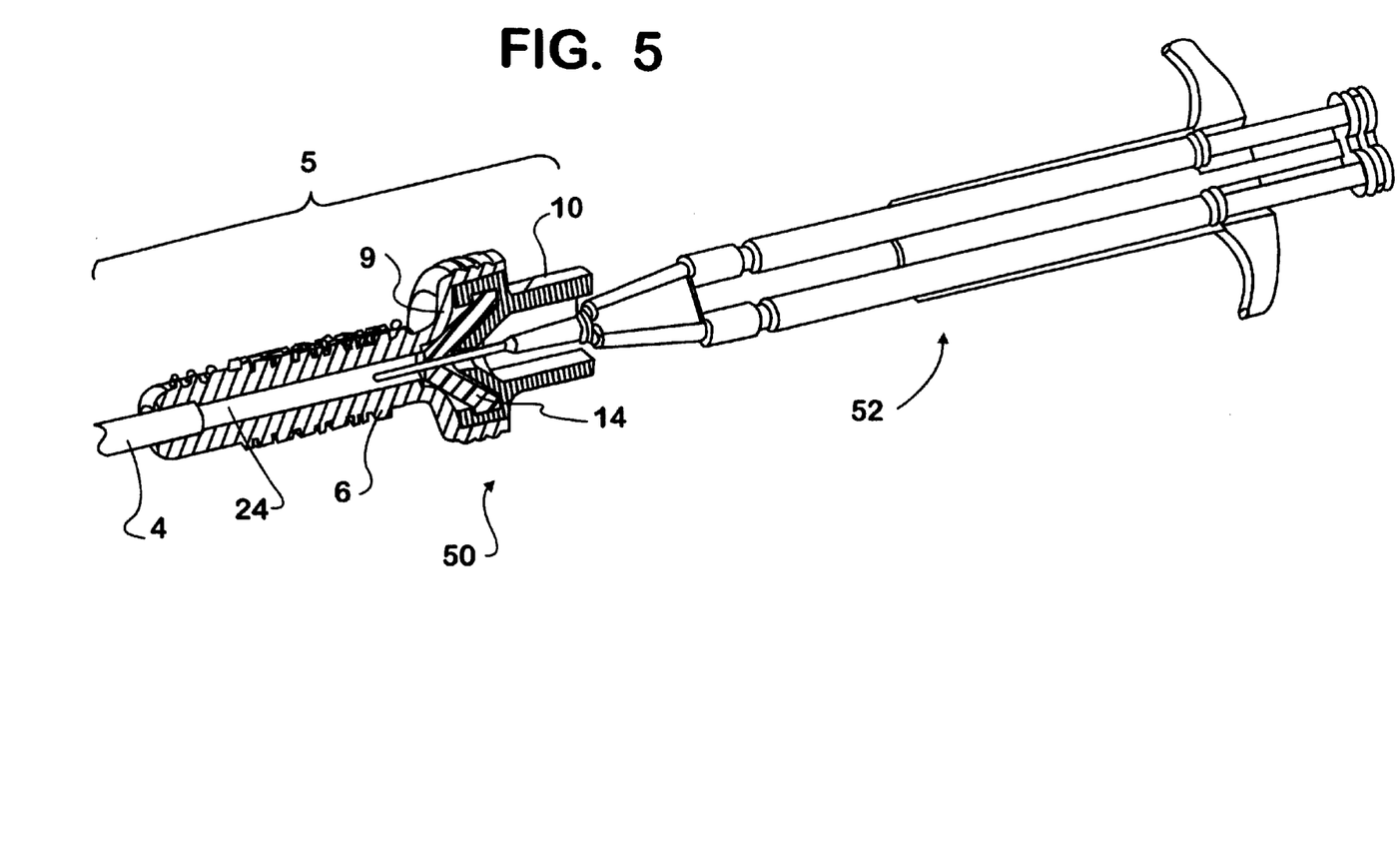
FIG. 5 is a perspective view of an alternative embodiment of a manual biopsy device according to the invention shown with the applicator device in place.

The hub housing 9 and the back housing 10 are preferably joined together using adhesive, glue, ultrasonic welding, a snap fit or by using equivalent joining means FIG. 5 illustrates another embodiment of the invention 50 with an applicator device 52 in place. In this embodiment, the substance supply tube 7 is eliminated. After the biopsy cannula 1 and needle member 2 have been withdrawn from the biopsy device, the surgical sealant is applied to the application channel 4 directly through the flow control member 14 and into the internal lumen 24 of the tube portion 6 where it flows into the application tube 4 for delivery to the biopsy site. This embodiment of the invention can also be used with a semi-automatic or automatic driver.

Figure 6:
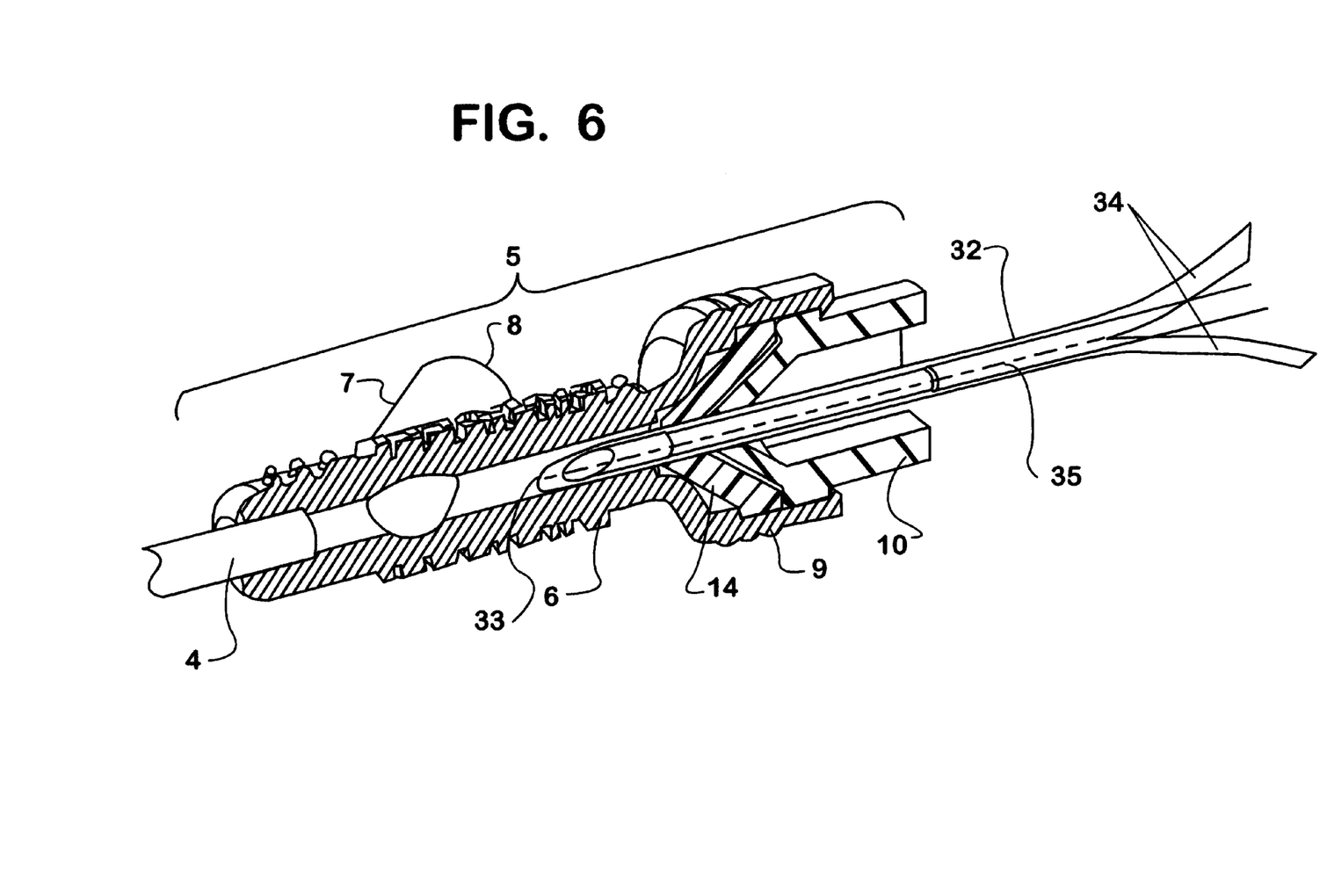
FIG. 6 is a sectioned view of the housing assembly of the biopsy device of FIG. 1 showing the split sheath protecting the flow control member as the biopsy needle set is passed through it.

FIG. 6 illustrates another embodiment of the invention in which the sharp tips 22 and 23 of the biopsy cannula 1 and the needle member 2 respectively are shielded by a split sheath 32 which covers the distal end of the biopsy needle set as it is inserted through the flow control member 14. The split sheath 32 has a distal end 33 which may be open or closed and a proximal end 34 which is affixed onto the biopsy cannula 1 by a hub or other affixation means. The split sheath 32 also has perforations 35 along each side of its length for removing the sheath from the biopsy needle set after it has passed through the flow control member 14.

The manual biopsy device of the invention 20 is used as follows. The user first prepares the patient for the biopsy procedure. Then, the substance or substances to be delivered to the biopsy site are prepared and loaded into the applicator device. For example, the substance may be the fibrin tissue sealant and application device described in U.S. Pat. Nos. 4,909,251 and 5,464,396 respectively which are incorporated by reference in their entirety herein.

The user next attaches the applicator device to the substance entry port 8 of the substance supply tube 7. In an alternative procedure, where greater maneuverability of the device in the surgical field is desired or required, the applicator device can be affixed to the substance entry port 8 after the biopsy sample has been collected and withdrawn from the device. If this procedure is used, the substance entry port should be plugged to prevent backflow or leakage of blood from the entry port.

The user guides the coaxially disposed application tube 4, biopsy cannula 1 and needle member 2 of the biopsy device to the biopsy site through the tissue with means well known in the art such as ultrasound, computerized tomography or magnetic resonance imaging equipment. Preferably, both the application tube 4 and the biopsy needle 1 have depth marks evenly spaced along their length to assist the user in identifying the exact location of the distal end of the device. The biopsy device is also preferably equipped with a depth stop that allows the user to lock the biopsy device if need arises.

After the biopsy device is accurately positioned, the needle member 2 is pushed forward into the tissue to be biopsied, allowing a sample of tissue to relax or prolapse into the recess or notch 3 cut out at the distal end. The biopsy cannula 1 is then pushed forward and the core of tissue caught in the notch cut or recess 3 is shorn off from the rest of the tissue by the cutting edge 22 of the biopsy cannula 1. The user then withdraws the biopsy needle set comprised of the biopsy cannula 1 and the needle member 2 proximally through the application tube 4, through the tube portion 6, through the flow control member 14 and through the back housing 10 until the complete needle set and the biopsy sample have cleared the flow control member 14 leaving only the application tube 4 in place at the biopsy site. After the biopsy cannula 1 and needle member 2 are withdrawn, the flow control member 14 will return to its normally closed position and will prevent blood or subsequently applied surgical sealant from exiting the device. The biopsy sample is now removed from the notch or recess 3 in needle member 2 and reserved for whatever analysis is appropriate to the sample. Alternatively, the user may collect an additional biopsy sample or samples by re-inserting the needle set into the device and repeating the procedure as required.

After the user has collected the final biopsy sample, surgical sealant is injected through the flow path beginning at the substance entry port 8, and extending down the substance supply tube 7, the distal end of the tube portion 6 and distally down the application tube 4 until it is delivered to the biopsy site. After an effective amount of tissue sealant is delivered to seal the biopsy site, the application tube 4 is slowly withdrawn from the tissue while simultaneously continuing to inject tissue sealant into the path traversed by the application tube 4 through the tissue. This withdrawal procedure allows a plug of tissue sealant to be deposited in the tissue in the track cut by the biopsy device.

In another embodiment of the invention 50 illustrated in FIG. 5, the biopsy sample is first collected as described above. After the user has collected the final biopsy sample and completely withdrawn the biopsy cannula 1 and needle member 2 from the application tube 4, surgical sealant is injected into the application tube 4 through the flow control member 14. After an effective amount of surgical sealant has been applied to the site, the application tube 4 can be withdrawn while continuing to inject surgical sealant as described above for embodiment 20.

In another embodiment of the invention illustrated in FIG. 6, the split sheath 32 protects flow control member 14 as the biopsy cannula 1 and needle member 2 are inserted through the flow control member 14. Once the needle tips 22 and 23 have cleared the flow control member 14, the split sheath 32 is peeled away from the needle assembly beginning at the proximal end of the sheath 34 and continuing down toward the distal end of the sheath 33 along the perforations 35 and withdrawn in two parts from the device as illustrated in FIG. 6. The biopsy sample or samples are then collected and the substance applied to the biopsy site as described below. The split sheath 32 can be used with any embodiment of the invention 20, 30, 40 or 50 set forth above or with the alternative embodiment for obtaining a tissue sample from an internal portion of a body by aspiration through a Menghini needle or equivalent soft tissue biopsy aspirating device In an alternate embodiment of the invention where a tissue sample is removed from an internal portion of the body by aspiration, surgical sealant is injected into the application tube 4 through the flow control member 14 after the Menghini needle or equivalent soft tissue biopsy aspirating device has been completely withdrawn from the application tube 4 and out the proximal end of the housing assembly 5. After an effective amount of surgical sealant has been applied to the site, the application tube 4 can be withdrawn while continuing to inject surgical sealant as described above for embodiment 20.

Although use of the device has been described in detail for the manual version of the device, one of ordinary skill in the art will be able to make the necessary adaptations to use the biopsy device and the described procedure with a semi-automatic or automatic biopsy device.

In addition to tissue sealant, other substances which may be advantageously applied to a biopsy site using the device of the invention include collagen-based hemostatic agents and any other surgical sealant or hemostatic agents.

While the invention has been ilustrated and described in detail in the drawings and foregoing description, the same is to be considered as illustrative and not restrictive in character. All changes and modifications that come within the spirit of the invention are contemplated as within the scope of the invention.

What is claimed is:

1. A device for delivering a substance to an internal portion of a body which has been acted on by a removable procedure performing instrument, said device comprising:

an application tube having a proximal end, a distal end and an internal lumen for receiving said substance and at least a portion of said instrument, said internal lumen distally terminating at a single opening located at the distal tip of said application tube;

a housing assembly disposed on the proximal end of said application tube and having a lumen extending from a proximal end of said housing assembly to a distal end of said housing assembly, said housing lumen being in communication with the internal lumen of said application tube so as to define a flow passage and through which said procedure performing instrument is slidingly moveable; and a flow control member disposed in said flow passage and having a portion that has a first position that opens said flow passage and a second position that closes said flow passage.

2. A device according to claim 1 wherein the flow control member is normally closed but openable by passage of the procedure performing instrument therethrough.

3. A device according to claim 2 wherein the flow control member is a duck-bill one-way valve.

4. A device according to claim 3 which further comprises an interface on said housing assembly engageable with the procedure performing instrument.

5. A device according to claim 4 wherein the interface on said housing assembly comprises prongs which engage a mating surface on the procedure performing instrument.

6. A device according to claim 3 wherein said procedure performing instrument comprises a biopsy cannula having an internal lumen and a distal cutting edge for cutting off tissue, a needle member slidably mounted within said lumen and having a recess for receiving said tissue sample; and a driver associated with said cannula and said needle for effecting relative movement between said cannula and said needle and cutting of said tissue.

7. A device according to claim 1 which further includes a substance supply tube extending from said housing assembly having a proximal end, a distal end and a lumen extending between said ends of the substance supply tube, said supply tube lumen communicating between said flow passage and being communicable with a substance supply.

8. A device according to claim 7 wherein the flow control member is normally closed but openable by passage of the procedure performing instrument therethrough.

9. A device according to claim 8 wherein the flow control member is a duck-bill one-way valve.

10. A device according to claim 9 which further comprises an interface on said housing assembly engageable with the procedure performing instrument.

11. A device according to claim 10 wherein the interface on said housing assembly comprises prongs which engage a mating surface on the procedure performing instrument.

12. A device according to claim 9 wherein said procedure performing instrument comprises a biopsy cannula having an internal lumen and a distal cutting edge for cutting off tissue, a needle member slidably mounted within said lumen and having a recess for receiving said tissue sample; and a driver associated with said cannula and said needle for effecting relative movement between said cannula and said needle and cutting of said tissue.

13. A device for obtaining a tissue sample from a body site and for applying at least one substance to said site said device comprising
- a biopsy cannula having an internal lumen and a distal cutting edge for cutting off tissue;
- a needle member slidably mounted within said lumen and having a recess for receiving said tissue sample;
- a driver associated with said cannula and said needle for effecting relative movement between said cannula and said needle and cutting of said tissue;
- an application tube having a proximal end, a distal end and an internal lumen said application tube being disposed around said cannula, the distal end of said application tube being rearwardly offset relative to the cutting edge of said cannula;
- a housing assembly sealingly engaging the proximal end of said application tube, said housing assembly including an internal lumen through which said cannula and said needle are slidingly moveable, said housing lumen being in communication with the internal lumen of said application tube so as to define a flow passage; and
- a flow control member disposed in said flow passage and having a portion that has a first position that opens said flow passage and a second position that closes said flow passage.

14. A device according to claim 13 wherein the flow control member is normally closed but openable by passage of said biopsy cannula and said needle member therethrough.

15. A device according to claim 14 wherein the flow control member is a duck-bill one-way valve.

16. A device according to claim 14 wherein said housing assembly includes a back housing engaging the proximal end of said housing assembly and being engageable with said driver, said back housing including a bore through which said biopsy cannula and said needle member are slidingly moveable.

17. A device according to claim 16 wherein said back housing includes prongs to engage with said driver.

18. A device according to claim 13 which further includes a substance supply tube extending from said housing assembly having a proximal end, a distal end and a lumen extending between said ends of the substance supply tube, said supply tube lumen communicating between said flow passage and being communicable with a substance supply.

19. A device according to claim 18 wherein the flow control member is normally closed but openable by passage of said biopsy cannula and said needle member therethrough.

20. A device according to claim 19 wherein the flow control member is a duck-bill one-way valve.

21. A device according to claim 20 wherein said housing assembly includes a back housing engaging the proximal end of said housing assembly and being engageable with said driver, said back housing including a bore through which said biopsy cannula and said needle member are slidingly moveable.

22. A device according to claim 21 wherein said back housing includes prongs to engage with said driver.

* * * * *